United States Patent [19]

Cho et al.

[11] Patent Number: 4,524,061

[45] Date of Patent: Jun. 18, 1985

[54] POLYMERIC SUNSCREENS

[75] Inventors: James R. Cho, Oakland; Stephen C. Johnson, Newton, both of N.J.

[73] Assignee: GAF Corporation, Wayne, N.J.

[21] Appl. No.: 487,484

[22] Filed: Apr. 22, 1983

[51] Int. Cl.³ .................... A61K 7/44; C08F 226/08
[52] U.S. Cl. .................................... 424/60; 424/78; 424/80; 424/81; 526/264; 526/310; 526/323
[58] Field of Search .................. 424/59, 60, 80, 78, 424/81, 7; 526/310, 323, 264

[56] References Cited

U.S. PATENT DOCUMENTS

| 3,330,730 | 7/1967 | Hernandez | 424/60 X |
|---|---|---|---|
| 3,529,055 | 9/1970 | Skoultchi et al. | 424/60 |
| 3,755,560 | 8/1973 | Dickert et al. | 424/60 |
| 3,795,733 | 3/1974 | Skoultchi et al. | 424/60 |
| 3,821,363 | 6/1974 | Black | 424/60 |
| 3,836,571 | 9/1974 | Skoultchi et al. | 424/60 X |
| 3,992,356 | 11/1976 | Jacquet et al. | 260/47 UA |
| 4,078,054 | 3/1978 | Isermann et al. | 424/60 |

Primary Examiner—Dale R. Ore
Attorney, Agent, or Firm—Marilyn J. Maue; Joshua J. Ward

[57] ABSTRACT

The polymeric sunscreen agents of the present invention comprise interpolymers of
(a) an olefinic p-aminobenzoate devoid of hydroxy substitution;
(b) N-vinylpyrrolidone;
(c) a monomer selected from the group consisting of a vinyl lactam having a number average molecular weight of at least 125, an acrylate or methacrylate or any mixture thereof and optionally
(d) acrylic or methacrylic acid.

13 Claims, No Drawings

POLYMERIC SUNSCREENS

This invention relates to a polymeric sunscreen agent as opposed to blends of ultraviolet light absorbers with polymeric carriers or low molecular weight compositions wherein the independent UV absorber is entrained or entrapped in the polymeric carrier and does not form an integral part of the polymeric structure. In one aspect the present invention relates to a polymeric compound which absorbs wavelengths of light in the range of from about 200 to 320 millimicrons which cause sunburn, while transmitting wavelengths in the range of from about 320 to 400 millimicrons which produce a desirable suntan. In another aspect, the present invention relates to a polymeric sunscreen having high skin substantivity or adhesion which resists removal by salt or fresh water but is easily removable upon the application of a mildly alkaline aqueous solution such as soap or shampoo. A third aspect of this invention relates to an interpolymeric sunscreen having a high viscosity such that the sunscreen product has a number average molecular weight of at least 1500 which resists crystallization on the skin under drying conditions and removal by salt water.

To overcome the deficiencies of sunscreen agent blends which are quickly removable upon contact with fresh or salt water, polymeric sunscreening agents have been proposed wherein the sunscreening agent is chemically bound in the polymeric backbone of the compound, thus making the compound more skin substantive. An example of such polymeric sunscreening agents is shown in U.S. Pat. No. 3,529,055 which employs a copolymer containing the sunscreening agent and a hydroxylated comonomer in a low viscosity or low molecular weight composition. Although polymeric sunscreening agents fulfill the primary function of absorbing the ultraviolet radiation which causes harmful sunburn, they are not sufficiently resistant to removal by salt water under extended periods of exposure and do not possess good adhesion to the skin when dry. This deficiency is caused by the presence of the hydroxylated monomer which is readily soluble in water and which dehydrates rapidly in the presence of the acidic monomer.

It an object of this invention to overcome the above deficiencies by providing an economical and efficient interpolymeric sunscreening agent having improved UV absorption properties, resistance to crystallization on drying and which is sufficiently resistant to attack by salt water for extended periods.

According to this invention there is provided an interpolymeric sunscreen agent comprising 3 or more monomers having the composition of:

(a) an olefinic p-aminobenzoate devoid of hydroxy substitution;
(b) N-vinylpyrrolidone;
(c) a monomer selected from the group consisting of a vinyl lactam having a number average molecular weight of at least 125, an acrylate or methacrylate or mixtures thereof; and optionally
(d) acrylic or methacrylic acid.

The polymers of this invention possess a specific viscosity of at least 0.05, which translates to a molecular weight above 1,400, up to about 0.9.

Suitable olefinic p-aminobenzoate monomers of the present polymer are those having the structure

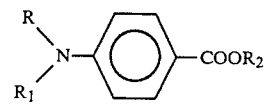

wherein
R is hydrogen or lower alkyl;
$R_1$ is hydrogen or lower alkyl and
$R_2$ is an aliphatic olefinic radical of 2 or 3 carbon atoms, i.e. vinyl or allyl. Examples of these monomers include N,N-dimethyl vinyl-p-aminobenzoate; N,N-dimethyl allyl-p-aminobenzoate; N-ethyl vinyl-p-aminobenzoate; N-ethyl allyl-p-aminobenzoate; N,N-diethyl vinyl-p-aminobenzoate; N,N-diethyl allyl-p-aminobenzoate; N-propyl-vinyl-p-aminobenzoate and N,N-dibutylvinyl-p-aminobenzoate and the like. It is to be understood that mixtures of the above monomers can be employed to comprise component (a) of the interpolymer. The hydroxylated compounds are excluded since the range of their absorption spectra are unsatisfactory for sunscreening.

Examples of suitable acrylate and lactam comonomers of the present polymeric compound are those having 4 to 30 carbon atoms and include glycidyl methacrylate or acrylate; methyl methacrylate or acrylate; ethyl methacrylate or acrylate; butyl methacrylate or acrylate; dimethylamino ethyl methacrylate or acrylate; amino ethyl methacrylate or acrylate; stearyl methacrylate or acrylate; lauryl methacrylate or acrylate; capryl methacrylate or acrylate; and ethylenically unsaturated lactams having the formula

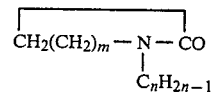

where m has a value of 3 to 5 and n has a value of 2 to 4, such as, vinyl caprolactam, N-allyl caprolactam, N-vinyl cyclohexamide, N-vinyl pyridone and the like. It is also to be understood that mixtures of these monomers can be employed as component (c) of the polymeric compound. Of these (c) monomers, those containing 5 to 24 carbon atoms and having the structure

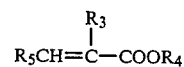

wherein $R_3$ is hydrogen or methyl; $R_4$ is alkyl having 2 to 12 carbon atoms or glycidyl and $R_5$ is hydrogen, amino or a mono- or di-lower alkyl substituted amino, are preferred; and of this group the mono- or di-methyl amino types are most preferred.

The weight ratio of monomers (a), (b) and (c) in the polymeric compound generally falls within the range of 10–50 wt. % monomer (a); 5–30 wt. % monomer (b) and 20–80% monomer (c) combined so as to form 100% of the polymeric compound; or when monomer (d) is included in the polymer, it comprises up to 40 wt. % of the total monomers in the polymeric compound. Generally, more or less of a certain monomer, within the above ranges, can be adjusted to meet the particular needs of a specific application.

The following monomer systems are particularly preferred:

1. N,N-dimethyl vinyl-p-aminobenzoate/vinylpyrrolidone/butyl acrylate/methacrylic acid in a wt. ratio of about 7.5/52.5/15/25.
2. N,N-dimethyl vinyl-p-aminobenzoate/vinylpyrrolidone/dimethyl amino ethyl methacrylate in a wt. ratio of about 20/60/20.
3. N,N-dimethyl vinyl-p-aminobenzoate/vinylpyrrolidone/lauryl methacrylate in a wt. ratio of about 10/15/75.
4. N,N-dimethyl vinyl-p-aminobenzoate/vinylpyrrolidone/vinyl caprolactam/dimethylamino ethyl methacrylate in a wt. ratio of about 10/24/61/5.

Broadly, the ratio of the UV monomer, i.e. component (a), to the total monomers in the polymeric compound is between about 0.001:1 and about 5:1, and is preferably between about 0.01:1 and about 1:1. The above monomer systems provide viscous liquid or liquifiable interpolymers having relatively high specific viscosities of at least 0.05, e.g. a molecular weight of at least 1500 and includes polymers of specific viscosity of up to 0.9, e.g molecular weight of up to about 5,000,000 or more; however the preferred specific viscosity range is between about 0.07 and about 0.8. Such high molecular weight compounds with their diversity in the monomer system provides particular advantages such as the formulation of a smooth continuous films on the skin without tendency to crystallize and maximum compatability with various types of liquid or aerosol carriers. Chemical bonding of the UV agent in the polymeric backbone which resists leaching of the UV component and high resistance of removal by salt water while exhibiting high solubility in alkaline soap solutions are additional advantages of the present polymeric sunscreening agents.

In general, the preparation of the present polymeric agents involves simply mixing the selected monomers and polymerizing them at a temperature between about 20° and about 175° C., preferably between about 40° and about 100° C., under a pressure from about 14 psig to about 1000 psig, preferably under atmospheric pressure, until the desired degree of polymerization is achieved, most usually for a period of from about 0.5 to about 10 hours, preferably from about 2 to 8 hours, in the presence of a free radical initiator such as a peroxide catalyst, for example butyl peroxide, benzoyl peroxide, hydrogen peroxide or an azonitrile compound, such as 2,2'-azo bis-(isobutyronitrile), 2,2'-azo-bis(2,4-dimethyl valeronitrile), etc. The polymerization may also be effected with an ionic catalyst or with stereo specific catalysts, such as a Ziegler catalyst. The polymerization is generally carried out in the liquid phase in a free radical initiated process utilizing bulk, solution, suspension or emulsion polymerization techniques wherein the reaction medium is water, alcohol, glycol, a glycol ester, benzene, ether, or ester such as ethyl acetate, acetone or an inert liquid hydrocarbon and polymerization is continued until a desired viscosity is achieved.

The polymeric product can be separated by precipitation and filtration, distillation, decantation, evaporation of solvent or any other convenient and conventional method to provide the viscous product.

It is preferred to carry out the polymerization reaction in the presence of a solvent for the monomers, but not for the resultant polymer. Such solvents are liquids in which no swelling or minimal swelling of the resultant polymer takes place. Thus, as the solubility of product formed during the polymerization decreases, a precipitate is formed which can easily be separated from the reaction mixture.

At the end of the reaction period, the reaction mixture is ordinarily allowed to cool to room temperature and the resultant crude product, which may be in solution or precipitated, is recovered as, for example, by filtration. The recovered product may be used in its unpurified, viscous crude form, or if desired, it may be subjected to purification by precipitation from suitable solvents such as aqueous alcohol, acetone or ether solutions to provide the viscous product.

Incorporation of these viscous polymeric sunscreen agents into suntan formulations, may be effected by a variety of procedures, depending upon the type of suntan formulation which is desired. For example, it is possible to prepare such formulations in the form of organic solvent solutions, aqueous emulsions, solid gels, or in "aerosol" formulations, which are dispersed under pressure as a spray by means of a propellant, usually halogenated hydrocarbon, carbon dioxide or a hydrocarbon gas, e.g. propane. It has been found desirable to prepare the polymeric sunscreen agent initially in the form of a solution or emulsion with an organic solvent such, for example, as ethanol or isopropanol. Such solutions or emulsions, upon the addition of various optional ingredients, may then be used directly or they may be converted into any of the above noted physical forms.

Illustrative of the various optional ingredients which may be included in suntan formulations are oils, fats, waxes, emulsifiers, surfactants, perfumes, silicone fluids, pigments, dyes, preservatives, etc.

In essence, the suntan formulations of this invention contains the sunscreen interpolymer admixed, dispersed or dissolved, with desired optional ingredients and a carrier which carrier is a cosmetically acceptable vehicle such, for example, as water, organic solvent, oil, fat, cream or gel, or any mixtures thereof. With respect to proportions, the suntan formulations should contain at least about 0.02% by weight of the polymeric compound or mixture of compounds wherein the UV absorbent monomer is present in an amount of between about 3 and about 70 wt. % of total monomers in the polymeric compound. Preferably, the present polymeric sunscreening compound is present in the final formulation at a concentration of between about 5 and about 25 wt. % of total monomers. The maximum concentration of ultraviolet absorbing compound will, of course, be dependent upon economic considerations as well as the degree of sunscreening which is required.

The present viscous polymers are also usefully formulated in the above concentrations in hair sprays, cosmetic lotions and creams or other products in which a polymeric film forming barrier to UV light between 200 and 320 millimicrons is desirable.

Having thus generally described the invention, reference is now directed to the following Examples which illustrate preferred embodiments but which are not to be construed as limiting to the scope of the invention as defined hereinabove and in the appended claims. All proportions and amounts in the Examples are by weight unless otherwise indicated.

EXAMPLE 1

Preparation of the copolymer of 7.5% N,N-dimethyl vinyl-p-aminobenzoate/52.5% vinylpyrrolidone/15% butylacrylate/25% methacrylic acid To a 250 ml three neck flask, equipped with a thermometer and a magnetic stirrer, was charged with 50 gms of distilled water, 0.5 gms of sodium lauryl sulfate and 0.05 gms ammonium persulfate at room temperature. The system was then purged with nitrogen and heated to 70° C., after which 2.625 gms of vinyl pyrrolidone, 0.75 gms of butylacrylate, 1.25 gms of methacrylic acid and 0.375 gms of vinyl-p-aminobenzoic acid were introduced into the flask with a syringe. The reaction mixture was maintained at 70° C. for 5 hours and then heated to 98° C. for an additional hour before cooling and discharging. The resulting copolymer has had a specific viscosity of 0.38 (1% in ethanol) which translates to a number average molecular weight greater than 50,000. The product was recovered as an aqueous emulsion. No further separation or purification was required.

Two microliters of the emulsion product was poured at room temperature onto a 1 cm$^2$ fetal pigskin swatch. The emulsion was glass rolled to a film of about 0.2 micron thickness. The swatch was then air dried for 2 hours. Upon examination, the dry film was homogeneous and showed good adhesion to the skin with no flaking or peeling. The swatch was not discolored.

The filmed swatch was then stuck with water to the surface of a 1 cm quartz UV cell and scanned with a UV spectrometer for UV absorption between 200 and 400 nm. Between 200-320 nm the film was found to provide 90% absorption. Above about 350 nm light was transmitted.

The swatch was then submerged in soap water for 5 minutes, whereupon the film was easily removed from the pigskin.

EXAMPLE 2

Preparation of the copolymer of 20% N,N-dimethyl vinyl-p-aminobenzoate/60% vinylpyrrolidone/20% dimethylamino ethyl methacrylate To a 250 ml three neck flask, equipped with a thermometer and a magnetic stirrer, was charged at room temperature, 12 gms of distilled N-vinyl-2-pyrrolidone, 4 gms of dimethylamino ethyl methacrylate, 4 gms of N,N-dimethyl vinyl-p-aminobenzoate, 0.1 gm of azobis(isobutyronitrile) and 50 ml of absolute ethanol. The contents was then purged with nitrogen for 5 minutes and heated to reflux. After 6 hours the mixture was cooled and discharged. The polymeric product was recovered as a viscous light yellow liquid having a specific viscosity of 0.286 in ethanol (1%).

Two microliters of the liquid was poured at room temperature onto a 1 cm$^2$ fetal pigskin swatch. The emulsion was glass rolled to a film of about 0.2 micron thickness. The swatch was then air dried for 2 hours. Upon examination, the dry film was homogeneous and showed good adhesion to the skin with no flaking or peeling. The swatch was not discolored.

The filmed swatch was then stuck with water to the surface of a 1 cm quartz UV cell and scanned with a UV spectrometer for UV absorption between 200 and 400 nm. Between 200-320 nm the film was found to provide 90% absorption. Above about 350 nm light was transmitted.

The swatch was then submerged in soap water for 5 minutes, whereupon the film was easily removed from the pigskin.

EXAMPLE 3

Preparation of the copolymer of 10% N,N-dimethyl vinyl-p-aminobenzoate/15% vinylpyrrolidone/75% lauryl methacrylate To a 250 ml three neck flask, equipped with a thermometer and a magnetic stirrer, was charged at room temperature, 50 gms of toluene and 0.25 gm of azobis(isobutyronitrile). The flask was then purged for 15 minutes with nitrogen and heated to 80° C., after which 0.75 gms of vinylpyrrolidone, 3.75 gms of lauryl methacrylate and 0.5 gm of N,N-dimethyl vinyl-p-aminobenzoate were introduced into the flask over a period of 1 hour. Then an additional 0.25 gm of azobis(isobutyronitrile) was added at 80° C. and the polymerization was carried out for 6 hours, whereupon the reaction mixture was cooled and discharged. The polymeric product was recovered as viscous liquid which is soluble in mineral oil having a specific viscosity of 0.09 in toluene (1%) which translates to a number average molecular weight greater than 3,000.

Two microliters of the liquid product was poured at room temperature onto a 1 cm$^2$ fetal pigskin swatch. The emulsion was glass rolled to a film of about 0.2 micron thickness. The swatch was then air dried for 2 hours. Upon examination, the dry film was homogeneous and showed good adhesion to the skin with no flaking or peeling. The swatch was not discolored.

The filmed swatch was then stuck with water to the surface of a 1 cm quartz UV cell and scanned with a UV spectrometer for UV absorption between 200 and 400 nm. Between 200-320 nm the film was found to provide 90% absorption. Above about 350 nm light was transmitted.

EXAMPLE 4

Preparation of the copolymer of 10% N,N-dimethyl vinyl-p-aminobenzoate/20% vinylpyrrolidone/61% vinyl caprolactam/5% dimethylamino ethyl methacrylate To a 250 ml three neck flask, equipped with a thermometer and a magnetic stirrer, was charged at room temperature, 50 gms of ethanol. The flask was then purged for 15 minutes with nitrogen, after which 0.025 gm of azobis(isobutyronitrile) was added and refluxed. Then 6.1 gms of vinyl caprolactam, 2.4 gms of vinyl-2-pyrrolidone, 0.5 gm of dimethylamino ethyl methacrylate and 1 gm of N,N-dimethyl vinyl-p-aminobenzoate were introduced into the flask over a period of one hour at reflux conditions and another 0.025 gm of azobis(isobutyronitrile) was added. The polymerization was carried out over a period of 6 hours after which the reaction mixture was cooled and discharged. The polymeric product is recovered as a viscous, light yellow ethanol solution having a specific viscosity of 0.185 (1% in ethanol).

Two microliters of the liquid product was poured at room temperature onto a 1 cm$^2$ fetal pigskin swatch. The emulsion was glass rolled to a film of about 0.2 micron thickness. The swatch was then air dried for 2 hours. Upon examination, the dry film was homogeneous and showed good adhesion to the skin with no flaking or peeling. The swatch was not discolored.

The filmed swatch was then stuck with water to the surface of a 1 cm quartz UV cell and scanned with a UV spectrometer for UV absorption between 200 and 400 nm. Between 200–320 nm the film was found to provide 90% absorption. Above about 350 nm light was transmitted.

The swatch was then submerged in soap water for 5 minutes, whereupon the film was easily removed from the pigskin.

EXAMPLE 5

Preparation of the copolymer of 10% vinyl-p-aminobenzoate/15% vinylpyrrolidone/75% lauryl methacrylate To a 250 ml three neck flask, equipped with a thermometer and a magnetic stirrer, was charged at room temperature, 50 gm of toluene and 0.25 gm azobis(isobutyronitrile). The flask was then purged with nitrogen and heated to 80° C. A mixture of 0.75 gm vinylpyrrolidone, 3.75 gm lauryl methacrylate and 0.5 gm of vinyl-p-aminobenzoate was fed into the flask gradually with a syringe over a period of one hour. Three hours after the first catalyst addition, another 0.25 gm of azobis(isobutyronitrile) was added. The total polymerization time was 6 hours. The polymeric product is recovered as a viscous liquid having a specific viscosity of 0.09 in 1% toluene which translates to a number average molecular weight greater than 3,000.

Two microliters of the above product was poured at room temperature onto a 1 cm$^2$ fetal pigskin swatch. The emulsion was glass rolled to a film of about 0.2 micron thickness. The swatch was then air dried for 2 hours. Upon examination, the dry film was homogeneous and showed good adhesion to the skin with no flaking or peeling. The swatch was not discolored.

The filmed swatch was then struck with water to the surface of a 1 cm quartz UV cell and scanned with a UV spectrometer for UV absorption between 200 and 400 nm. Between 200–320 nm the film was found to provide 90% absorption. Above about 350 nm light was transmitted.

The swatch was then submerged in soap water for 5 minutes, whereupon the film was easily removed from the pigskin.

EXAMPLE 6

Preparation of the copolymer of 10% vinyl-p-aminobenzoate/10% vinylpyrrolidone/80% lauryl methacrylate To a 250 ml three neck flask, equipped with a thermometer and a magnetic stirrer, was charged at room temperature, 45 gm of toluene, 5 gm of isopropanol and 0.025 gm of azobis(isobutyronitrile). The flask was then purged with nitrogen and heated to 80° C. A mixture of 0.5 gm vinylpyrrolidone, 4.0 gm of lauryl methacrylate and 0.5 gm vinyl-p-aminobenzoate was fed into the flask gradually with a syringe over a period of one hour. Three hours after the first catalyst addition, another 0.025 gm of azobis(isobutyronitrile) was added. The total polymerization time was 6 hours. The polymeric product is recovered as viscous liquid having a specific viscosity of 0.12 in 1% ethanol.

Two microliters of the above product was poured at room temperature onto a 1 cm$^2$ fetal pigskin swatch. The emulsion was glass rolled to a film of about 0.2 micron thickness. The swatch was then air dried for 2 hours. Upon examination, the dry film was homogeneous and showed good adhesion to the skin with no flaking or peeling. The swatch was not discolored.

The filmed swatch was then stuck with water to the surface of a 1 cm quartz UV cell and scanned with a UV spectrometer for UV absorption between 200 and 400 nm. Between 200–320 nm the film was found to provide 90% absorption. Above about 350 nm light was transmitted.

The swatch was then submerged in soap water for 5 minutes, whereupon the film was easily removed from the pigskin.

The excellent sunscreen properties found for the above polymeric compounds can be achieved with the other polymers of this invention. For example, the following aminobenzoates can be substituted for component (a) in any of the above examples.

N,N-dimethyl allyl-p-aminobenzoate
N-ethyl vinyl-p-aminobenzoate
N-propyl vinyl-p-aminobenzoate
N,N-diethyl allyl-p-aminobenzoate Also other acrylates, methacrylates or lactams can be substituted for component (c) in any of the above examples. Particularly preferred are 50/50 butyl acrylate/methylamino ethylacrylate
50/50 stearyl methacrylate/stearyl acrylate
25/75 N-vinyl pyridone/dimethylamino ethyl acrylate
40/60 N,N-diethylamino ethyl acrylate/N,N-diethylamino octyl methacrylate
dimethylamino decyl acrylate
diethylamino heptyl methacrylate
propylamino hexyl acrylate The UV light absorption efficiency of sunscreen materials on fetal pigskin stratum corneum at wavelength λ and Eλ is defined as $$E\lambda = \frac{\frac{\text{(Absorbance of } S.C. \text{ with 2 } \mu l/cm^2 \text{ sunscreen)}}{\text{Absorbance of } S.C. \text{ at } \lambda}}{\text{(Absorbance of sunscreen at 2 } \mu l/ml \text{ in solution) at } \lambda}$$

The Eλ (Efficiency at 310 nm) reflects the true UV absorbing ability of a UV absorber at wavelength λ on fetal pigskin stratum corneum relative to the maximum UV absorption in solution. The Eλ value for the above examples is as follows:

| EXAMPLE | Eλ |
| --- | --- |
| 1 | 0.64 |
| 3 | 0.78 |
| 4 | 0.45 |
| 5 | 0.78 |
| 6 | 0.54 |

The above sunscreening results were compared with several commercial sunscreening agents: Sample A, supplied by Johnson and Johnson, Inc. as SUNDOWN, which is a mixture of a polymer binder with 7% octyl-dimethyl-p-aminobenzoic acid, 5% octyl salicylate and 2% oxybenzone in an emollient base, in which the sunscreen agent has a molecular weight less than 300; and Sample B which is 4% p-aminobenzoic acid in ethanol as a UV absorber having a MW less than 150. The UV light absorption efficiency, determined as outlined above on fetal pigskin, was:

| SAMPLE | Eλ |
| --- | --- |
| SAMPLE A | 0.09 |

| SAMPLE | Eλ |
|---|---|
| SAMPLE B | 0.046 |

It can be seen that the UV absorption efficiency at wavelength of 310 nm for sample A and sample B is much lower than that found for the polymers of Examples 1, 3, 4, 5 and 6.

EXAMPLE 7

The UV absorbance at 310 nm wavelength of 5 samples of fetal pigskin stratum corneum were measured by a UV spectrophotometer. A 10% mineral oil solution of 10% vinyl-p-aminobenzoate/15% vinylpyrrolidone/75% lauryl methacrylate polymer was prepared and 1 microliter of the polymer solution was applied to each of four 1 cm² samples of the pigskin with a micro-pipette. The UV absorbance of these coated samples was then measured by a UV spectrophotometer and the average of the four samples was recorded. The efficacy of the coating on the pigskin is the difference between the coated and uncoated samples. The present coating showed an average of 98% efficiency.

The above coated fetal pigskin samples were each suspended in a beaker containing 100 milliters of distilled water and stirred for a total of 30 minutes. The amount of polymer left on the sample was determined after 15 minutes and again after 30 minutes of immersion. Results of this experiment are reported in the following Table.

A 50/50 ethanol-water solution of 10% Carboset 514* (an anionic acrylic resin binder of B. F. Goodrich) and 1% p-aminobenzoic acid mixture was prepared and 1 microliter of this solution of UV absorber/binder admixture was applied by micro-pipette to the fifth 1 cm² sample of pigskin stratum corneum. The sample was then dried in air for 1 hour, after which it was suspended in a beaker containing 100 ml distilled water and stirred for a total of 30 minutes. The amount of sunscreen left on the sample was determined at 15 minutes and 30 minutes as measured by a UV spectrophotometer and results reported in the following Table.
* Chemical Abstract Registry No. 25133-97-5

TABLE

| | Resistance to Removal by Water | |
|---|---|---|
| | Sun Screen Agent | |
| | Polymer Coated Pigskin Sample | Admixture Coated Pigskin Sample |
| % of sunscreen agent applied to pigskin | 100 | 100 |
| % of sunscreen agent remaining after 15 min. water wash | 74 | 45 |
| % of sunscreen agent remaining after 30 min. water wash | 60 | 45 |

The above results show that the sunscreen of the present invention wherein the UV agent comprises a monomer of the polymeric compound is far superior to the mixture of UV agent which is physically incorporated with a polymeric binder. When 10% vinyl-p-aminobenzoate is admixed with 90% Carboset 514, the resistance to water removal is about the same as shown for the above admixture.

What is claimed is:

1. The polymer consisting essentially of the monomers:
   (a) 10 to 50 wt. % of a p-amino-alkenylbenzoate having the formula

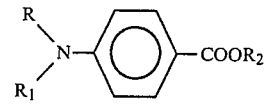

wherein R is hydrogen or lower alkyl, $R_1$ is hydrogen or lower alkyl and $R_2$ is a vinyl or allyl radical;
   (b) 5 to 6 wt. % of N-vinylpyrrolidone;
   (c) 20 to 80 wt. % of a monomer selected from the group consisting of an acrylate or methacrylate having 5 to 24 carbon atoms or a lactam having the formula

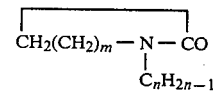

wherein m has a value of 3 to 5 and n has a value of 2 to 4; and mixtures thereof; and optionally containing
   (d) 0 to 40 wt. % of acrylic or methacrylic acid based on the total of monomers (a), (b) and (c).

2. The polymer of claim 1 wherein component (a) is N,N-dimethyl vinyl-p-aminobenzoate.

3. The polymer of claim 1 wherein component (c) is a lactam.

4. The polymer of claim 1 wherein component (c) is a butyl acrylate.

5. The polymer of claim 3 wherein component (c) is a vinyl caprolactam.

6. The polymer of claim 1 wherein component (c) is a dimethylamino ethyl methacrylate.

7. The polymer of claim 1 wherein component (c) is a lauryl methacrylate.

8. The polymer of claim 1 wherein component (c) is a mixture of a lactam and a dimethylamino alkyl methacrylate.

9. The polymer of claim 1 wherein component (d) is present in an amount of between about 5 and about 40 weight % of monomers (a), (b) and (c).

10. The polymer of claim 9 wherein component (d) is present in an amount up to 25 weight % of monomers (a), (b) and (c).

11. A sunscreening formulation comprising an effective amount sunscreening amount of the polymer of claim 1 having a specific viscosity of from about 0.05 to about 0.9 and an inert cosmetically acceptable carrier.

12. The sunscreening formulation of claim 11 containing from about 0.02 to about 25 wt. % of said polymer.

13. The sunscreen formulation of claim 11 wherein the p-amino-alkenylbenzoate of the polymer is N,N-dimethyl vinyl-p-aminobenzoate and component (c) of the polymer contains at least a major portion of N,N-dimethylamino ethyl methacrylate.

* * * * *

UNITED STATES PATENT AND TRADEMARK OFFICE
CERTIFICATE OF CORRECTION

PATENT NO. : 4,524,061
DATED : June 18, 1985
INVENTOR(S) : James R. Cho et al

It is certified that error appears in the above-identified patent and that said Letters Patent is hereby corrected as shown below:

Column 10, line 16, Claim 1, "5 to 6 wt.% of N-vinylpyrrolidone" should read -- 5 to 60 wt. % of N-vinylpyrrolidone --.

Signed and Sealed this

Twelfth Day of August 1986

[SEAL]

Attest:

DONALD J. QUIGG

Attesting Officer

Commissioner of Patents and Trademarks